(12) United States Patent
Drocourt et al.

(10) Patent No.: US 7,384,762 B2
(45) Date of Patent: Jun. 10, 2008

(54) PROCESS FOR TRAPPING AND CONFINING MICROORGANISMS IN AIR USING WATER-SOLUBLE POLYMERS

(75) Inventors: Jean-Louis Drocourt, Yerres (FR); Les Dodd, Surrey (GB); Andrew I. Cooper, Liverpool (GB); Philippe Cornet, Noiseau (FR)

(73) Assignee: Chemunex, Ivry Sur Seine (FR)

( * ) Notice: Subject to any disclaimer, the term of this patent is extended or adjusted under 35 U.S.C. 154(b) by 0 days.

(21) Appl. No.: 10/443,878

(22) Filed: May 23, 2003

(65) Prior Publication Data

US 2004/0043453 A1    Mar. 4, 2004

Related U.S. Application Data

(63) Continuation of application No. PCT/EP01/14773, filed on Nov. 23, 2001.

(30) Foreign Application Priority Data

Nov. 24, 2000   (EP) ................... 00403304

(51) Int. Cl.
*C12Q 1/24* (2006.01)
(52) U.S. Cl. .......................... 435/30; 435/31
(58) Field of Classification Search ............... 424/405; 435/71.2, 7.2; 436/546
See application file for complete search history.

(56) References Cited

U.S. PATENT DOCUMENTS 4,664,857 A * 5/1987 Nambu .................. 264/28
4,774,957 A * 10/1988 Nambu et al. ............. 600/414
5,855,652 A    1/1999 Talley

FOREIGN PATENT DOCUMENTS

| DE | 0845480 A1 * | 3/1998 |
| DE | 0816513 A1 * | 7/1998 |
| EP | 0 845 480 A1 | 6/1998 |
| GB | 1 441 576 | 7/1976 |

OTHER PUBLICATIONS

Sigma Chemical Co. St. Louis, MO. 1995. Polyvinyl Alcohol, p. 853.*
Aldrich Chemical Company, Inc Catalog 1994, pp. 1177 and 1181).*
Monitoring Airborne Microorganisms During Food and Beverage Processing, Millipore Corporation—Technical Brief (retrieved from the internet on May 11, 2001), p. 2; middle column; figure 2.
New Brunswick Slit-to-Agar Biological Air Sampler, product information, Website of the New Brunswick Scientific Corpration (retrieved on May 11, 2001).
"Rompp: Lexikon der Biotchnologie und Gentechnik", 1999, Georg Thieme Verlag, Stuttgart-New York, pp. (with partial English translation), english translation only considered.

* cited by examiner

*Primary Examiner*—Patricia A. Duffy
(74) *Attorney, Agent, or Firm*—Birch, Stewart, Kolasch & Birch, LLP

(57) ABSTRACT

A process for trapping and confining microorganisms in air using water-soluble polymers is disclosed. The water-soluble polymers are readily soluble in water or a physiological diluent, have reasonable mechanical strength so that they can be transported without rupture, retain water and adhere to microorganisms. A process for the rapid and sensitive detection of microorganisms in air under aseptic conditions is also disclosed.

3 Claims, 1 Drawing Sheet

PROCESS FOR TRAPPING AND CONFINING MICROORGANISMS IN AIR USING WATER-SOLUBLE POLYMERS

This application is a Continuation of PCT International Application No. PCT/EP01/14773 filed on Nov. 23, 2001, which published as WO 02/42410 on May 30, 2002, in English and which designated the United States and on which priority is claimed under 35 U.S.C. § 120, the entire contents of which are hereby incorporated by reference.

FIELD OF THE INVENTION

The present invention relates to a process for trapping and confining microorganisms in air using water-soluble polymers. More specifically, the water-soluble polymers can be used as a vehicle in maintaining viable and non-viable microorganisms for further analysis. A rapid and sensitive process for providing the number of microorganisms present in air for sterility testing is also disclosed.

BACKGROUND OF THE INVENTION

Polymers consist of chains of repeat chemical units that occur naturally or by the virtue of their chemistry, they can be adapted to form synthetic polymers by control of the chemical structure and weight.

Synthetic polymers are made by the chemical reaction of monomers to form long polymer chains. The two primary variables that affect the physical properties of synthetic polymers are the chemical nature of the monomer repeat units and the molecular weight of the polymer, which can be precisely controlled. Thus, it is known that polymers with higher molecular weights possess greater mechanical strength, but are much more viscous in solution.

By varying the ratio of chemical groups within the polymer, one can adjust the physical properties of the polymer for particular applications. For instance, the mechanical strength and solubility of the polymers can be adjusted in this manner.

By blending different types of polymers, characteristics of the finished copolymer can exhibit optimized characteristics. By design and synthesis of specific polymers, materials can be generated with the exact properties required for a specific function. For example, by specific treatment, the surface area of a polymer plate (90 mm) can be increased from 1 meter squared to 1,500 meter squared. This single process will increase the physical and biological characteristics of the polymer into a more efficient mechanism for recovery of environmental organisms.

Water-soluble polymers are known in the art and are described by Prokop et al in "Water Soluble Polymers for Immunoisolation I: Complex Coacervation and Cytotoxicity" in *Advances in Polymer Science*, 136: pgs. 53 to 73 (1998). These polymers have a multitude of uses such as artificial hearts, as immunoisolation barriers, for pain control for terminal cancer patients and in the encapsulation of pancreatic islets.

Besides their medical uses, polymeric material is also used in laboratories in many of the supplies such as tests tubes, sample wells, pipette tips, disposable pipettes and the like.

For instance, as a solid support, various polymers were used in a method for detecting DNA in a cell, while preserving the morphology of the nucleus as described in U.S. Pat. No. 5,501,954. In this method the DNA was deposited onto a polymeric membrane filter, incubated with a fluorescently labeled sample and detected using a labeled probe. The polymeric membranes utilized were made of polycarbonate, polyvinylidene fluoride, polysulfone, nylon, cellulosic esters, nitrocellulose and Teflon® (PTFE). The polymeric membranes described in this patent are water-insoluble polymers, since one of the requirements for this method is that the polymeric membranes must retain the cellular material through a series of treatments and washings and still remain intact.

EP 546 032 describes a method for immobilizing molecules, polymers or microorganisms by mixing with an aqueous solution dispersion of a polymer and applying the mixture to a coherent film. The membranes formed are water insoluble and can be stored dry.

The analysis of microorganisms is important in many different areas, for instance, in food preparation, drinking water, for pharmaceutical applications in drug production, for cosmetic analysis, in electronic industries and in the analysis of medical applications.

Samples for the testing of various microorganisms are generally collected using cotton swabs, for example, and sent to a laboratory for analysis. The analysis process requires that the samples first are cultured.

Alternatively rapid methods for analysis of microorganisms are also known in the art using biosensors. For example, WO 9931486 discloses biosensors having a polymer film coated with a metal and a patterned receptor layer printed onto the coated metal on which there is a receptive material that specifically binds analyte. The amount of microorganism that was attached to the biosensor was measured via a diffraction image upon irradiation with a laser.

Another type of biosensor is disclosed in WO 982747 which comprises a polymer film coated with a metal and a self-assembling monolayer having a receptive material on it specific for an analyte, printed onto the film. The self-assembling monolayer is printed in a pattern, so that, when the biosensor binds the analyte and the biosensor diffracts transmitted light to form a pattern.

It should be appreciated that although biosensors can detect various microorganisms in the environment measuring a diffraction pattern is often inaccurate, imprecise and lacks sensitivity.

Moreover, determination of the number of active microorganisms rather than total counts is of great importance in many areas of microbiology. Unfortunately, it is widely recognized that conventional culture techniques underestimate the fraction of, true viable microorganisms and that total counts, showing all microorganism particles, overestimate this fraction.

Besides the problems associated with obtaining an accurate number of microorganisms present in a sample, it is also known that culturing techniques on a growth medium are time-consuming and generally require between about eighteen hours and twenty days to obtain a result. The use of traditional growth medium is non-specific and natural, therefore variable and non-controlled.

One method that overcomes the requirement for the culturing of microorganisms after they are sampled is described in EP 0 816 513A1. This reference discloses the use of a pressure sensitive adhesive sheet for collecting microorganisms on surfaces that may contain the microorganism. The adhesive sheet is composed of a laminate of an adhesive layer mainly composed of a water soluble polymer and a water permeable membrane which does not permit the passage of microorganisms. Hence, EP 0 816 513A1 requires that at least two layers of the adhesive sheet be bonded together, one layer of which acts to capture the microorganisms in a process after sampling.

Moreover, the sampling of the microorganism with the pressure sensitive adhesive sheet requires that the adhesive layer be brought in contact with the surface of a test object such that accumulation of microorganisms is accomplished on the sheet Hence, even visual observation of microorganisms is accomplished using a chromagenic agent which is present in the adhesive layer or in water, which method cannot be very sensitive.

EP 0 816 513 A1 does not disclose or suggest that either their device to sample, requiring at least two laminated layers, and/or their method to detect microorganisms can be used for sterility testing of air samples in which very high sensitivity of detection is required.

Indeed, it is well known in the art that specific monitoring and control of aseptic environments is required for the processing of drugs, dosage forms and in certain cases medical devices. A large portion of sterile products are manufactured by aseptic processing since this process relies on the exclusion of microorganisms from the process stream and the prevention of microorganisms from entering containers during filling. Aseptic processing is generally performed in clean rooms and the environment is always carefully monitored.

Besides the use of aseptic conditions in the pharmaceutical industry, the electronic industry also uses and monitors clean rooms for the manufacture of electronic components, computer chips, computer components and the like.

The difference between these two industries in environmental monitoring is that in the electronic industry nonviable microorganisms or particulates are generally measured and there is less emphasis on the number of viable particulates or microorganisms. In contrast, in the pharmaceutical industry there is a much greater concern with respect to the point of viable microorganisms.

One method of monitoring in aseptic conditions is to ascertain the total particulate count. This method does not provide information concerning the microbiological content of the environment. The basic limitation of particulate counters is that they only measure particles of 0.5 µm or larger. While airborne particles are not free-floating or single cells, they frequently associate with particles of 10 µm to 20 µm and hence solely testing for particulate counts without microbial counts is discouraged.

It is known in the art that clean rooms must meet particular standards. In fact specifications for air changes per hour and velocities, although not included in federal standards, are customary. Thus, for example class 100,000 rooms in aseptic processing environments are designed to provide a minimum of 20 air changes per hour, while class 100 clean rooms provide more than 100 air changes per hour. By diluting and removing contaminants, large volumes of air are likely to reduce airborne contamination in aseptic production.

There are certain air cleanliness guidelines that must be met for the different grades of a clean room. Thus, for example, for class 100, the running mean of all data points must be <1 colony-forming unit (cfu) per cubic meter of air and at least 85% of all samples taken must be zero. For class 10,000 clean rooms, at least 65% of all the samples taken must be zero and for class 100,000 at least 50% of samples must be zero. Thus, these values are very critical in order to provide safe environmental monitoring.

There are many methods known in the art to sample viable airborne microorganisms such as the slit-to-agar sampler, the sieve impactor, the centrifugal sampler the surface air system sampler and the gelatin filter sampler. All of these samplers require a pump, motor or vacuum that either pulls or pushes air through the sampling unit The use of these "active" sampling devices can be inconvenient where there is space limitation in the clean room since they may occupy needed space. Moreover, these devices may also be a hazard to safe aseptic conditions, since they can disrupt directional air flow as a result of the size and location of the instrument or of the manner in which the equipment forces air into the sampling media or filter.

Another type of "non-active" sampling devices is settling plates. Setting plates are an easy and inexpensive way to qualitatively assess the air environment over long periods of time. Settling plates consist of agar which are placed in Petri dishes and are useful in critical areas where the use of an active sampling device is obstructive. In fact settling plates, when exposed for four to five hour periods, may provide a limit of detection similar to those observed with active sampling devices.

However, in many of these methods, agar is used as the medium to capture the microorganisms and it is known that agar shortages, as well as product variability have led to a search for suitable substitutes for agar.

Furthermore, it is well known in the art that the monitoring of microorganisms under aseptic conditions is not as yet perfected. Variations in sampling sensitivity and limits of detection can be attributed not only to the inherent characteristics of the sampling method itself, but also to media variability, incubation temperatures, sample handling and accidental contamination of the samples.

Moreover, microbial assessment of dean rooms is performed using methods that do not result in a quantitative assessment Rather, the methods used can be at best defined as semiquantitative. In fact many methods are only suitable to measure the presence of a typically high levels of microbial contamination and their accuracy and precision is very poor.

Therefore, there is a need in the art of environmental analysis of microorganisms to provide not only a rapid method of analysis for air samples, but also a means to accomplish this analysis with greater accuracy, especially in the sterility testing area.

Thus, it is an object of the present invention to overcome the problems associated with the prior art.

It is an object of the present invention to use water-soluble polymers to trap and confine microorganisms in air.

It is another object of the present invention to provide a sensitive means for sterility analysis of air samples.

It is another object of the present invention to provide a polymer that has sufficient mechanical strength so that it can be transported, is soluble in water or other physiological diluents, retains water to a certain degree while maintaining live microorganisms in a viable status and can capture microorganisms from the air.

It is yet another object of the present invention to provide a process for rapidly detecting microorganisms in an unknown air sample.

It is a further object of the present invention to provide a process to detect microorganisms in an unknown air sample which does not require that the microorganism be subjected to further growth.

It is another object of the present invention to provide a process in which the variable and uncontrolled system of using growth medium is avoided.

These and other objects are achieved by the present invention as evidenced by the summary of the invention, description of the preferred embodiments and the claims.

SUMMARY OF THE PRESENT INVENTION

The invention relates to a process for trapping and confining microorganisms in air for analysis, said process comprising the steps of:
(a) casting a water-soluble polymer; and
(b) subjecting said water-soluble polymer to a microorganism present in the air.

Another aspect of the present invention provides a process for detecting and counting down to one the number of microorganisms in the air in an aseptic environment, said process comprising the steps of:
(a) trapping and confining said microorganisms present in the air with a water-soluble polymer;
(b) dissolving said water-soluble polymer in a diluent to form a solution;
(c) separating said microorganisms from said solution; and (d) detecting said microorganisms by fluorescence using a SCAN RDI® or a D-COUNT® analyzer.

DETAILED DESCRIPTION OF THE PREFERRED EMBODIMENTS OF THE INVENTION

Figure 1:
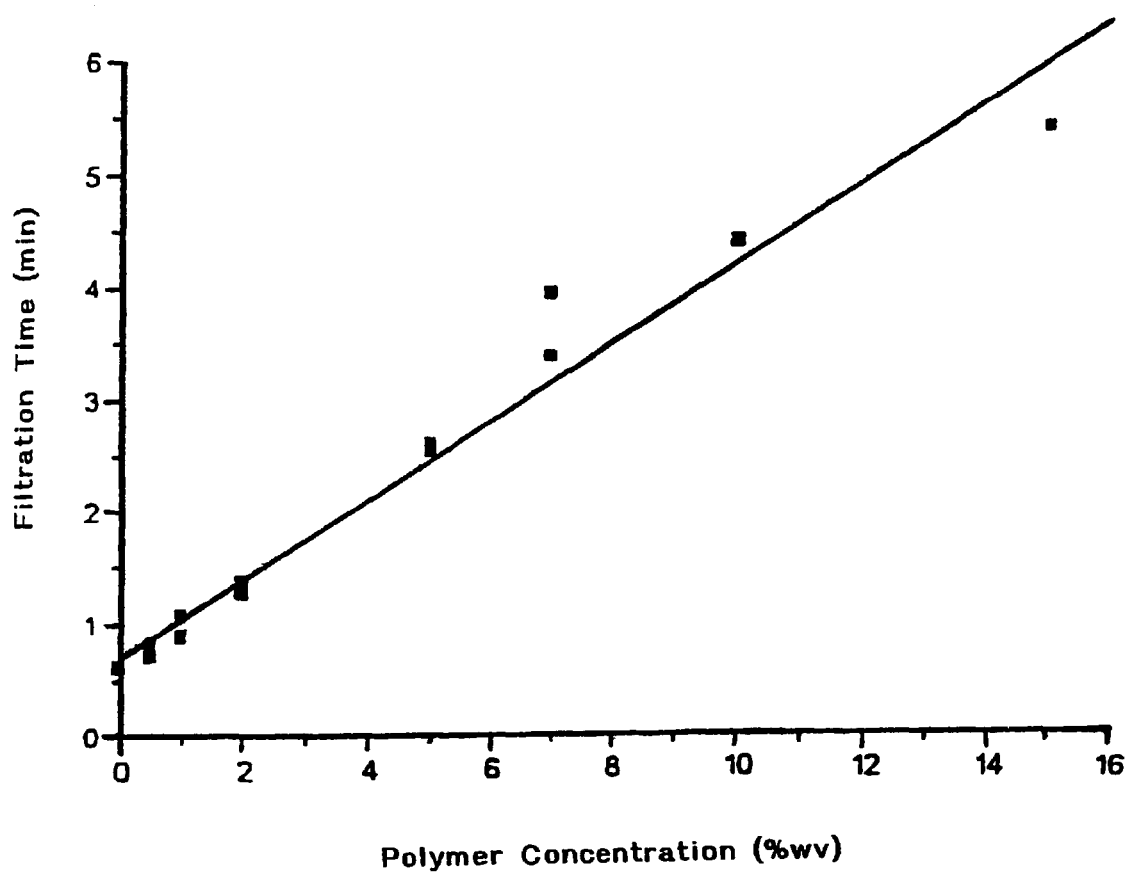
FIG. 1 is a graph illustrating the variation in filtration time with the concentration of the polymer poly(vinyl alcohol) (PVA) (K30) using a 0.4 µm porosity membrane (CB04).

As used herein, the term "microorganism" encompasses algae, bacteria, fungi (yeast, molds and mold spores) (including lichens), rickettsiaea, protozoa, pollen, parasites, acariens, viruses and subviral agents.

As used herein, the term "bacteria" encompasses spore forming bacterial and includes, but is not limited to, *Escherichia coli*, Brucella, Shigella, Clostridia, *Bacillus anthracis, Bacillus subtilis, Staphylococcus epidermidis*, Treponema, Leptospira, Borrelia, *Vibrio fetus, Spirillum minus*, Staphlococci, Streptococci, Gonococci, Salmonella, Meningococci and the like, as well as *Staphylococus aureus, Listeria monocytogenes, Candida albicans, Pseudomonas aeruginosa, Aspergillus niger, Mycobacterium phlei, Shigella sonnei*, Zymomonas sp, *Edwardsiella ictalui* and the like.

As used herein, the term "water-soluble polymers" means that the polymers are soluble in water and/or physiological diluents, have sufficient mechanical strength so that the polymer can be transported, retain water to a certain degree, and adhere to microorganisms.

By "viable microorganisms" is meant that the microorganisms are capable of living under appropriate conditions.

By "appropriate conditions" is meant that the microorganisms are not desiccated or not stressed.

By "trap" is meant that the microorganisms are sequestered from the environment by the water-soluble polymers.

By "confining" is meant that the microorganisms adhere to or are otherwise trapped by the water-soluble polymers.

By "the environment" is meant surroundings whether they be air, physical objects, surfaces, and the like.

As used herein the terms "SCANRDI®" and "CHEMSCANRDI®" are used interchangeably and are the same instrument. It is well known in the art that in the U.S.A. the instrument is referred to as "SCANRDI®", while in Europe it is referred to as "CHEMSCANRDI®".

More specifically, the present invention relates to a process to trap and confine microorganisms that are present in the air by using a water-soluble polymer. Preferably the present invention involves the environmental analysis of microorganisms present in, for example, a clean mom wherein aseptic conditions have to be maintained. After the microorganisms are trapped and confined they can be further transported to a laboratory for further analysis.

The microorganisms that are trapped and confined may be viable microorganisms, non-viable microorganisms and mixtures thereof. In a preferred embodiment of the present invention, viable microorganisms are trapped and confined in the air using water-soluble polymers. The viable microorganisms are then transported and subject to analysis.

After the microorganisms are collected on the water-soluble polymer, they are analyzed using a SCANRDI® or a D-COUNT® analyzer. The use of these particular analyzers provides a count of the microorganisms within approximately 90 minutes from receipt of the sample and can measure the presence down to one microorganism present in the air with the SCANRDI® analyzer. The sensitivity of this type of analysis is extremely important for monitoring microorganisms that may be present in aseptic processing such as in clean rooms. Furthermore, there is no need to culture the microorganisms prior to analysis, thereby saving time and expense.

The water-soluble polymers used in the present invention should be adaptable to environmental analysis and should be prepared with well-defined and reproducible physical properties. Furthermore, the water-soluble polymers used in the present invention should be readily soluble in water and/or a physiological diluent, have reasonable mechanical strength so that they can be transported without rupture, retain water to a certain degree that the microorganisms that are trapped and confined may be viable upon analysis and adhere to microorganisms in the air.

It is preferred that the water-soluble polymers have a high surface area morphology for sufficient microorganism capture, are non-toxic, have good film forming properties or molding properties, processability, filterable after dissolution, are non-bactericidal and preferably sterilizable, if desirable.

The water-soluble polymers used in the present invention may be natural or synthetic. If natural polymers are used, they can be modified to achieve the specific characteristics set forth above by, for example, polymer grafting or oxidation. It is preferred that structurally well-defined water-soluble polymers are used in the process to trap and confine the microorganisms.

The polymers used in the present invention can be water-soluble homopolymers, water-soluble copolymers, blends of more than one homopolymer/copolymer, porous polymers and the like. These polymers can be designed and synthesized to generate the specific properties described above.

More specifically, the water-soluble polymers of the present invention are characterized by their mechanical strength; i.e., they can be transported without rupture and thus have a particular molecular weight which is within the range of 500 to 500,000 g/mol, preferably 2, 000 to 250,000 g/mol, more preferably 1,000 to 100,000 g/mol.

Furthermore, the water-soluble polymers must be soluble in water and/or other physiological diluents, which characteristic is dependent upon the molecular weight and the degree of hydrolysis, if applicable. The particular molecular weights which are encompassed by this solubility criteria are set forth above. As far as the degree of hydrolysis is concerned, if applicable, the water-soluble polymers of the present invention have a degree of hydrolysis between 70% to 90%, preferable between 75% to 90% and most preferably between 80 to 89%.

Moreover, the water-soluble polymers of the present invention must retain water to a certain degree. This characteristic can be measured by the water equilibrium content when these polymers are cast and air dried. More particularly, the water equilibrium content should be between 1% to 50% w/w, more preferably 2% to 40% w/w and most preferably 4% to 30% w/w.

Due to the above properties of mechanical strength, hydrophilicity and water retention, the water-soluble polymers of the present invention, adhere to microorganisms, as exemplified in the examples. Thus, microorganisms present in the air can be easily trapped and confined with the water-soluble polymers set forth in the present invention.

In a preferred embodiment, the polymers used in the present invention may also have the following properties:

(1) the polymer powder should be readily soluble in an appropriate diluent at ambient temperature;

(2) they should have film forming or molding properties and can be cast as a uniform film or in a mold;

(3) they should have good mechanical properties and ideally be easily removed from the container in which they are cast without breaking;

(4) the polymer films, molds, beads or microspheres should dissolve completely in water at ambient temperatures over a reasonable time scale;

(5) the polymer films, molds, beads or microspheres should dissolve to form clear, homogenous solutions in water which are filterable through membranes;

(6) no interfering polymer residue should remain on the membrane after filtration;

(7) the polymer should be non-bactericidal;

(8) the polymer film, mold, beads or microspheres should be adhesive towards microorganisms;

(9) preferably, the polymer should be thermally stable up to 120° C.; i.e., stable under autoclaving conditions or inert towards irradiation;

(10) the polymer must retain water; and

(11) the polymer should not be chemically cross-linked to form an insoluble gel, upon sterilization.

Examples of the polymers that can be used in the present invention can be porous or water-soluble synthetic polymers. Porous polymers can be prepared, for example, using the procedure of Yang and Zhang, *Journal of Membrane Science*, 114, pgs. 149-155 (1996). Water-soluble synthetic polymers include, but are not limited to, polyethylene oxide (PEO), polyethylene glycol (PEG), poly(vinyl pyrrolidone) (PVP), poly(vinyl alcohol) (PVA), poly(acrylic acid) (PAA), poly(acrylic acid)-sodium salt (PAMPSA), poly(sodium styrene sulfonate (PSSS), polyacrylamide, agarose, poly(hydroxy ethyl methacrylate (PHEMA), poly(hydroxy ethyl acrylate (PHEA) and the like.

Two copolymers or blends of more than one homopolymer/copolymer can also be utilized. The polymer can also be tailored or modified to change the various properties of the polymer as desired; i.e., for example to increase or decrease their mechanical strength, water-solubility characteristics, microorganism retention quality, water retention quality and combinations thereof.

In a most preferred embodiment of the invention, it is preferable to use as the water-soluble polymer between 1,000 to 250,00 g/mol, more preferably between 5,000 to 100,000 g/mol, most preferably between 7,500 g/mol to 25,000 g/mol of poly(vinyl alcohol) (PVA); 5,000 to 500,000 g/mol, more preferably 10,000 to 100,000 g/mol and most preferably 20,000 to 75,000 g/mol poly(vinyl pyrrolidone) (PVP); between 500 to 100,000 g/mol, more preferably between 1,000 to 50,000 g/mol, most preferably between 2,000 to 10,000 g/mol polyethylene oxide (PEO); between 2,000 to 250,000 g/mol, more preferably between 5,000 to 100,000 g/mol, most preferably between 10,00 to 50,000 g/mol poly(acrylic acid) (PM); between 1,000 to 250,000 g/mol, more preferably between 2,000 to 100,000 g/mol, most preferably 5,000 to 50,000 g/mol poly(acrylic acid)sodium salt (PAMPSA); and between 500 to 500,000 g/mol, more preferably 1,000 to 50,000 g/mol, most preferably 1,500 to 10,000 g/mol polyacrylamide.

In a most preferred embodiment of the present invention, it is preferable to use poly(vinyl alcohol) (PVA) with an average molecular weight in the range of 10,000 to 100,000 g/mol and a degree of hydrolyses in the range of 80% to 90%.

The polymers can be shaped in the form of films, swabs, plates, fibers, disks, contact plates, microspheres, beads and the like. The shape of the polymer is not important and can be adapted to the environment in which air sampling is needed. All of these shapes can be adapted using porous or non-porous polymers.

If the water-soluble polymers are shaped in the form of a flat object, such as a film, plate or disk, the thickness of the polymer may vary in a range between 50 μm and 5 mm. It is preferred to have the thickness in a range between 50 μm to 1 mm.

When microspheres or beads are desired methods of extrusion or emulsion/suspension which are known in the art can be used. For example, microspheres can be prepared by the method of Thanoo et al, *J. Pharm. Pharmacol*. 45, 16 (1993).

The size of the microspheres may vary depending upon the amount of microorganism that needs to be trapped and confined. The size may range from 50 nm to 3 mm, more preferably from 1 μm to 1 mm, most preferably 250 μm to 500 μm.

The water-soluble polymers can be cast from solution according to known methods in the art. For example, the polymer powder can be dissolved in a diluent and sterilized, if desired.

The diluent that is generally used to dissolve the water-soluble polymer is generally bacteria free water. However, phosphate buffered saline, distilled water, deionized water, WFI water, sterile water and mixtures thereof can also be utilized. If necessary, the pH of the polymer solution can be adjusted using dilute acetic acid or sodium hydroxide to the desired pH, such as a neutral pH.

If sterilization is desired, any sterilization method can be used as long as the water-soluble polymers retain their water solubility, mechanical strength, are not desiccated and maintain their trapping and confining capabilities such that the microorganisms survive in the water-soluble biopolymer. More specifically, the polymers can be sterilized using an autoclave (121° C. for 15 minutes), by gamma irradiation (at a dose of between 10 K Gray to 30 K Gray, preferably 20 K Gray) or by using ethylene oxide treatment.

The water-soluble polymer solution can be filtered through a polyester membrane to dean up the water soluble polymer solution. Generally a 0.3 μm to 0.6 μm, preferably 0.4 μm to 0.5 μm, more preferably a 0.45 μm membrane is used.

After sterilization, the diluted water-soluble polymer is then formed into an appropriate shape as described above and is cast by letting the solution evaporate at ambient temperature or in a laminar fume hood.

In general, the water-soluble polymer concentrations during casting range from about 1% to 20% by weight, preferably 1% to 12% by weight, more preferably from 5% to 10% by weight. When using two copolymer or blends of more than one homopolymer/copolymer, the same final concentration is used. For example, a copolymer mixture of 1% poly(vinyl alcohol) and 4% by weight poly(vinyl pyrrolidone) can be used.

In a typical procedure, an aliquot of the water-soluble polymer can be cast. For example, 5 ml of a 10% polymer solution can be added to a Petri dish and the water is allowed to evaporate at room temperature in a laminar flow hood in order to cast the water-soluble polymer.

The water-soluble polymer should be preferably prepared and cast under clean and dust free conditions.

"Generally", for air monitoring the water-soluble polymers are cast in Petri dishes having a size of between 90 mm to 150 mm of diameter, more preferably between 50 mm to 130 mm of diameter. Generally, a larger amount of polymer is needed in air sampling than in other environmental applications such as the monitoring of microorganisms on surfaces.

After the polymers are cast, the water-soluble polymer is exposed to air wherein microorganisms are trapped and confined. The sample is preferably collected under sterile conditions by methods known in the art.

For example, if one wants to measure the amount of microorganisms in a particular surrounding or room, the casted water-soluble polymer can be left in the surrounding or room for between 1 to 10 hours, preferably 1.5 to 8 hours, more preferably 2 to 4 hours. The water-soluble polymer acts as a trap and confines the microorganisms in the polymer.

Alternatively, the water-soluble polymer can be attached to a suitable frame and hung in front of a ventilation shaft.

After the unknown sample is placed or trapped and confined on the water-soluble polymer, the water-soluble polymer with the unknown sample is then resuspended in a diluent such as peptone and 0.1% Tween80®, or WFI water, bacterial free water, sterile water, phosphate buffered saline and the like.

The trapped microorganisms can be recovered by centrifugation or by filtration. In a preferred embodiment, the filtration step is used. The resuspended polymer solution can be filtered through membranes of between 0.1 microns to 5 microns, preferably 0.2 microns to 4.5 microns, most preferably 0.4 microns.

The content in the number of microorganisms of the resuspended polymer solution is determined using the D-COUNT® analyzer (Chemunex) or using a SCANRDI® analyzer (Chemunex) described in U.S. Pat. No. 5,663,057, incorporated herein by reference. By using these two analyzers, the number of microorganisms present in the sample can be analyzed within 90 minutes and does not require that the microorganisms be grown prior to analysis. Both analyzers are cytometers that use laser beams in the analysis.

In this preferred embodiment, the resuspended polymer solution containing the microorganism can be analyzed with the SCANRDI®. The sample is then filtered through a 0.4 micron porosity membrane.

The microorganisms that are retained on the surface are labeled either by adding directly the labeling solution in the samples for the D-COUNT® analyzer or the SCANRDI® analyzer. The microorganisms that are retained on the surface of the filtration membrane after sample filtering are labeled using a fluorescent marker or any chemical, which generates fluorescence.

Fluorescent labels that can be used in the present invention include, but are not limited to fluorescent dyes based on fluorescein derivatives such as ChemChrome V, but other kinds of fluorescent markers such as Cascade Blue LUCIFER YELLOW® OREGON GREEN®, Acridine Orange, and the like.

In this preferred embodiment the ChemChrome V is used putting the membrane retaining microorganisms in contact with the ChemChrome V solution, which has been prepared in the following way:

100 µl of ChemChrome V was added to 10 ml of filtered (0.22 µm) ChemSol labeling buffer. The solutions were completely mixed.

After incubating the membrane with fluorescent dye, according to the protocols described in WO98/55861, the membranes are then analyzed with the SCANRDI® analyzer. After analysis, the amount of fluorescent events detected by the analyzers correlates to the number of microorganisms in the sample.

In order to further illustrate the present invention and advantages thereof, the following specific examples are given, it being understood that the same are intended only as illustrative and in nowise limitative.

EXAMPLES

Example 1

Preparation of Polymers

Preparation of Poly(Vinyl Alcohol) (PVA) Films 5 g of poly(vinyl alcohol)(CAS No. 9002-89-5) having an average molecular weight of 10,000 g/mol and a degree of hydrolysis of 80% was dissolved in water (100 cm$^3$) while stirring at room temperature. When fully dissolved this solution was then autoclaved. 20 ml of the solution was added to a sterile plastic Petri dish. The film was then cast in air by allowing the water to evaporate at ambient temperature in a laminar flow fume hood. The time for film casting to occur was about 10 hours depending on the laminar air flow conditions. Equilibrium water content in the films as measured in the procedure set forth above was around 6 wt. %.

Preparation of Poly(Vinyl Pyrrolidone) (PVP) Films 5 g of poly(vinyl pyrrolidone) (CAS No. 9003-3908) and having an average molecular weight of 44,000 g/mol was dissolved in water (1.00 cm$^3$) while stirring at room temperature. When fully dissolved this solution was then filtered through a 0.45 micron filter. A 1% solution was added to a sterile plastic Petri dish. The film was then cast in air by allowing the water to evaporate at room temperature in a laminar flow fume hood. The time for film casting to occur was about 16 hours.

Example 2

Water Content and Physical Properties of the Polymers

Films were cast from aqueous solutions at a range of concentrations varying from 5% to 10%; i.e., 5 g to 10 g polymer in 100 ml water. 5 ml of a 10% polymer solution was added to a small Petri dish and the water was allowed to evaporate at room temperature and ambient pressures. Films were removed intact from the Petri dishes and the mechanical properties of the films were evaluated by measuring the time taken for the water-soluble polymer to dissolve, as well as the filtration time.

Thus, the films were redissolved in pure water (50 ml at 20° C.) and the time taken for dissolution was noted.

Filtration tests were carried out on all water soluble polymers (50 ml solutions) at three different concentrations of 1, 2 and 5% under standard conditions (400 mbar) using two different filtration membranes having a pore size of 0.2 microns and 0.4 microns, respectively.

Equilibrium water content was established for some of the cast films, since this was considered to be an important in determining water retention. The films were cast in air by the usual method being diluted with water and subjected to a laminar fume hood for drying and then left until the samples reached a constant weight. The samples were then dried in a vacuum oven at 100° C., again until the samples reached a constant weight From these measurements, an equilibrium water content may be calculated from the difference in mass between the two constant weights, which is equal to the mass of water; i.e., mass-dry weight.

Example 3

Cytotoxicity Studies

The above polymer solutions, namely PVA or PVP, were resuspended in 50 ml of prefiltered peptone (1 g/liter) and 0.1% Tween 80®. About 10 to $10^3$ of the following microorganisms were added to the resuspended polymer solution in separate tubes:

The above polymer solutions, namely PVA or PVP, were resuspended in 50 ml of prefiltered peptone (1 g/liter) and 0.1% TWEEN 80®. About 10 to $10^3$ of the following microorganisms were added to the resuspended polymer solution in separate tubes:

*E. coli, S. aureua, P. aeruginosa, B. subtilis, C. albicans* and *A. niger.*

10 ml of each of the polymer/microoganisms were then analyzed using the SCAN RDI® using the protocols of "TCV" and "Fungi" which were developed by Chemunex and are commercialized with the SCAN RDI®.

For Detecting Bacteria, Bacterial Snores and Yeast.

CSE/2 Counterstain.

With a syringe (20 ml) fitted with a needle, the CSE/2 bottle cap was pierced and CSE/2 (1 ml per sample) was aspirated. A 0.2 µm Autotop unit filter was fitted to the syringe and 1 ml of this counterstain was dispensed into the filter funnel. The vacuum tap was opened and the CSE/2 was allowed to pass through the filter. When complete (no liquid remained on the surface of membrane but the membrane should remain damp) the vacuum tap was dosed. The vacuum was then released.

Pre-Labeling of Samples

The sample carrier was prepared placing the Labeling Pad supports in position. A labeling Pad from the packaging was removed and 600 µl of ChemSol A4 (Activation medium) was then deposited on the labeling Pad.

The sample membrane was transferred to the Labeling Pad ensuring the same face of the membrane was in contact with the Labeling Pad as with the filter.

The Labeling Pad and membranes were incubated at 37° C.±3° C. for 60 min.±5 min.

Labelling of the Samples

After the prelabeling stage the Chemfilter membrane was transferred to a new labeling Pad previously soaked with 600 µl of the labeling solution and incubated for 30 minutes at 30° C. according to the protocols described in WO 98/55861.

SCAN RDI® analysis

After the labeling step, the labeled Chemfilter membrane was introduced into the SCAN RDI® instrument. The analysis was performed in the four minutes following the introduction of the membrane in the machine.

The labeled Chemfilter membrane from the Labeling Pad was transferred onto the Support Pad. The membrane holder protected in a Petri dish was transferred to the ChemScan instrument. The scan was initiated using the software. The analysis was performed in the four minutes following the membrane holder preparation.

The fungi protocol is set forth below:

Fungi—For Detection of Yeast and Moulds.

CSE/5 Counterstain.

With a syringe (20 ml) fitted with a needle, the CSE/5 bottle cap was pierced and CSE/5 (1 ml per sample) was aspirated. A 0.2 µm Autotop unit filter was fitted to the syringe and 1 ml was dispensed into the filter funnel.

The vacuum tap was opened and the CSE/5 was allowed to pass through the filter. When complete (no liquid remained on the surface of membrane but the membrane should remain damp) the vacuum tap was dosed. The vacuum was then released.

Pre-Labeling of Samples

A labeling Pad from the packaging was removed and 600 µl of ChemSol A6 (Activation medium) was then deposited on the labeling Pad. The sample membrane was transferred to the Labeling Pad ensuring the same face of the membrane was in contact with the Labeling Pad as with the filter.

The Labeling Pad and the membranes were incubated at 30° C.±3° C. for 3 hrs±5 min.

Labeling of Samples

After the prelabeling stage, the Chemfilter membrane was transferred to a new labeling Pad previously soaked with 600 µl of the labeling solution and incubated for 1 hr at 37° C.±3° C. according to the protocols described in WO 98/55861.

A fresh Labeling Pad for the labeling stage was prepared. The Labeling Pad was placed onto a Labeling Pad support on the ChemPrep S. 600 µl of labeling solution was placed onto the Labeling Pad.

The Chemfilter membrane was transferred to the new Labeling Pad.

The Labeling Pad and membrane were then transferred in the sample carrier to the ChemPrep S and incubated at 37° C.±3° C. for a minimum of 1 hr to complete the incubation.

SCAN RDI® analysis

After the labeling step, the labeled Chemfilter membrane was introduced into the SCAN RDI® instrument. The analysis was performed in the four minutes following the introduction of the membrane in the machine.

Controls using the microorganisms alone which had no contact with the polymer were also analyzed as described above. The results are shown in Table 1 below.

TABLE 1

| | Control (no contact with polymer) | | PVA | | PVP | |
|---|---|---|---|---|---|---|
| | Chem | | | | Chem | |
| n = 2 | Scan result | % recovery | ChemScan result | % recovery | Scan result | % recovery |
| E. coli | 114 | 110 | 130 | 126 | 113 | 111 |
| S. aureus | 67 | 129 | 85 | 120 | 68 | 109 |
| P. aerugi nosa | 49 | 127 | 49 | 98 | 51 | 120 |
| B. subtilis | 81 | 138 | 87 | 156 | 87 | 192 |

TABLE 1-continued

| | Control (no contact with polymer) | | PVA | | PVP | |
|---|---|---|---|---|---|---|
| | Chem | | | | Chem | |
| n = 2 | Scan result | % recovery | ChemScan result | % recovery | Scan result | % recovery |
| C. albicans | 148 | 130 | 147 | 132 | 147 | 129 |
| A. niger | 60 | 132 | 55 | 101 | 58 | 116 |

In the above Table 1, the percent recovery is the ratio between the Scan RDI® results and the plate counts.

Example 4

Additional Cytotoxicity Studies

The preparation of the polymers was performed in Example 2. The same procedure was performed as in Example 3, except the microorganisms were contacted with the polymers for 15 minutes prior to analysis. The results of this experiment are set forth in Table 2.

TABLE 2

| | Control (no contact with polymer | | PVA | | PVP | |
|---|---|---|---|---|---|---|
| | Chem Scan result | % recovery | Chem Scan result | % recovery | Chem-Scan result | % recovery |
| E. coli | 38 | 136 | 44 | 140 | 44 | 124 |
| S. aureus | 52 | 146 | 63 | 134 | 55 | 115 |
| C. albicans | 49 | | 62 | | 64 | |

As can be seen from the results, the recoveries were greater than 100% and are very similar to the control.

Example 5

Measurement of Microorganisms in Air

In this experiment, the number of microorganisms in the air was measured. The polymer PVA was prepared as in Example 2 and left in the laboratories respectively 30 minutes and 3 hrs 30 minutes prior to analysis. The analysis was performed as set forth in Example 3. Table 3 gives the results of this experiment.

TABLE 3

| Sampling site and conditions FVA biopolymer | ChemScan results bacteria/membrane | Petri dish cfu/me membrane (TCS, 7 days) |
|---|---|---|
| Lab 1:30 minutes contact | 48 | 17 |
| | 42 | 24 |
| | 42 | |
| Lab 2:3 hrs 30 contact | 8 | 19 |
| | 12 | 16 |
| | 14 | 22 |

Example 6

Testing of Additional Polymers

Polyethylene oxide (PEO), polyethylene glycol (PEG), poly(acrylic acid)(PAA), poly(acrylic acid-sodium salt) (PAMPSA), poly(sodium styrene sulfonate) (PSS) and polyacrylamide are prepared according to Example 2 and cast following the, procedure in Example 1. Cytotoxicity studies are performed as in Examples 3 and 4. The number of microorganisms is analyzed according to Example 5. Similar results are obtained using these particular polymers.

Example 7

Microorganisms Measured in a Clean Room

In this experiment, the number of microorganisms in the air is measured in a class 100 clean room. The polymers were prepared as in Example 2 and cast in a Petri dish of 90 mm of diameter. The casted water-soluble polymer is then placed by the air duct during operational conditions and left for 4 hours prior to analysis. The analysis was performed as set forth in Example 3.

Since no microorganisms are present in this sample it is confirmed that the clean room meets the air cleanliness standards in this particular controlled environment.

Example 8

Detection of Total Population of Microorganisms with Orange Acridine: Counting of Viable and Dead Cells with the SCAN RDI®.

The above polymer solutions, namely PVA or PVP were prepared as in Example 2 and cast in a Petri dish of 90 mm diameter.

About 10 to $10^3$ microorganisms of a mix (50×50) of viable and killed microorganisms are laid on the surface of the casted water-soluble polymer.

Then the polymer films are removed from the plates and redissolved in pure water as described in Example 2.

The polymer's solutions containing the microorganisms are filtered through the 0.4 μm Chemfilter membranes before these latter are processed further with the following labeling protocols:

- the number of viable microorganisms is defined using the viability marker (ChemChrome) and SCAN RDI® analyzer according to the TCV protocol as described in the previous examples.
- the total cell population (live and dead) of microorganisms is determined using the following protocol: 0.8 ml of Orange Acridine solution was laid on the surface of the Chemfilters membranes and incubated for two minutes at room temperature. The number of labeled cells is then obtained following manual observation on the membranes with a conventional epifluorescence microscope.

The results show a perfect coherence between the number of viable cells determined by the SCAN RDI® analyzer, the expected number of killed cells and the value of the whole population which has been experimentally determined.

While the invention has been described in terms of various preferred embodiments, the skilled artisan will appreciate that various modifications, substitutions, omissions and changes may be made without departing from the scope thereof. Accordingly, it is intended that the scope of the present invention be limited solely by the scope of the following claims, including equivalents thereof.

What is claimed is:

1. A process for trapping and confining microorganisms in air for analysis, said process comprising the steps of:
   (a) casting a water-soluble polymer;
   (b) placing said water-soluble polymer in an area to be monitored for microorganisms; and
   (c) collecting microorganisms present in the air on said water soluble polymer, wherein said water-soluble polymer has a degree of hydrolysis between 70% to 90% and a water equilibrium content between 1% to 50% w/w % and is soluble in water or other physiological diluents.

2. The process according to claim 1, wherein said water-soluble polymer has a water equilibrium content between 2% to 40% w/w.

3. The process according to claim 1, wherein said water-soluble polymer has a water equilibrium content between 4% to 30% w/w.

* * * * *